United States Patent [19]

Kozak

[11] Patent Number: 5,434,301
[45] Date of Patent: Jul. 18, 1995

[54] METHODS FOR RECOVERY OF ACIDS

[75] Inventor: William G. Kozak, Hatfield, Pa.

[73] Assignee: Henkel Corporation, Plymouth Meeting, Pa.

[21] Appl. No.: 160,349

[22] Filed: Dec. 1, 1993

Related U.S. Application Data

[63] Continuation-in-part of Ser. No. 115,382, Sep. 1, 1993, abandoned.

[51] Int. Cl.$^6$ .............................. C07C 143/24
[52] U.S. Cl. ........................ 562/96; 562/89; 562/90; 562/91; 562/88
[58] Field of Search .................. 562/89, 90, 91, 96, 562/88

[56] References Cited

U.S. PATENT DOCUMENTS

| | | | |
|---|---|---|---|
| 2,141,569 | 12/1938 | Tucker | 106/27 |
| 2,415,558 | 2/1947 | Hesler et al. | 260/535 |
| 2,543,659 | 2/1951 | Durant | 23/149 |
| 2,899,460 | 8/1959 | Sias et al. | 562/96 |
| 3,015,655 | 1/1962 | Stark | 260/211 |
| 3,083,146 | 3/1963 | Sweeney et al. | 562/96 |
| 3,193,575 | 7/1965 | Nebel et al. | 260/505 |
| 3,244,620 | 4/1966 | Hansen et al. | 210/22 |
| 3,277,162 | 10/1966 | Johnson | 260/505 |
| 3,371,112 | 2/1968 | Winstrom et al. | 260/535 |
| 3,720,707 | 3/1973 | Vanderlinden et al. | 562/96 |
| 3,859,349 | 1/1975 | Cody | 260/535 |
| 3,927,081 | 12/1975 | Thomas, Jr. et al. | 562/96 |
| 3,954,491 | 5/1976 | Adrian et al. | 106/100 |
| 3,983,170 | 9/1976 | Shozo et al. | 260/535 |
| 4,194,952 | 3/1980 | Bodenbenner et al. | 203/12 |
| 4,673,507 | 6/1987 | Brown | 210/681 |
| 4,720,579 | 1/1988 | Kulprathipanja | 562/580 |
| 4,772,749 | 9/1988 | Karrenbauer et al. | 562/580 |
| 4,851,573 | 7/1989 | Kulprathipanja et al. | 562/580 |
| 4,851,574 | 7/1989 | Kulprathipanja | 562/580 |
| 5,068,419 | 11/1991 | Kulprathipanja | 562/580 |

FOREIGN PATENT DOCUMENTS 1264293  6/1970  United Kingdom ................. 562/96

OTHER PUBLICATIONS

B. A. Bolto and L. Pawlowski, *Wastewater Treatment by Ion Exchange*, pp. 49–56 (E. & F. N. Spoon, Ltd, N.Y., N.Y., 1987).

R. C. Glogau, "Separate Sulfonic and Sulfuric Acids with an Ion Exchange Resin", *Industrial and Engineering Chemistry*, vol. 53, pp. 275–278 (Apr. 1961).

"Chemical Processing By Ion Exchange", Form No. 17 424, pp. 1–18 (Dow Chemical U.S.A., Midland, Mich. 1978).

(List continued on next page.)

Primary Examiner—Marianne M. Cintins
Assistant Examiner—Keith MacMillan
Attorney, Agent, or Firm—Wayne C. Jaeschke; John Daniel Wood; Daniel S. Ortiz

[57] ABSTRACT

A process for recovering sulfuric acid from a mixture containing sulfuric acid and organic sulfonation products is provided. The process comprises contacting a mixture comprised of sulfuric acid and (i) a naphthalene-based material selected from the group consisting of naphthalenesulfonic acids, lower-alkyl substituted naphthalenesulfonic acids, and mixtures of two or more of such materials, or (ii) an aromatic-based carbonyl condensate (preferably a material selected from the group consisting of formaldehyde condensates of naphthalenesulfonic acids, formaldehyde condensates of lower-alkyl substituted naphthalenesulfonic acids, and mixtures of two or more of such materials), with a basic anion exchange resin in essentially the sulfate form (and preferably in the form of essentially non-porous particles) to provide a raffinate liquid phase enriched with respect to said mixture in said naphthalene-based material and depleted with respect to said mixture in sulfuric acid. The raffinate liquid phase is removed from contact with the resin. The resin is then contacted with an aqueous liquid at an essentially neutral pH to form an extract liquid phase consisting essentially of sulfuric acid and removing said extract liquid phase is removed from contact with the resin.

42 Claims, No Drawings

OTHER PUBLICATIONS

"Dowex Ion Exchange Resins; Powerful Chemical Processing Tools", Form 177-1395-87, pp. 1-12 (Dow Chemical U.S.A., Midland Mich., 1979.

E. A. Knaggs, "Sulfonation and Sulfation", *Encyclopedia of Chemical Technology*, vol. 22, 1-45 (John Wiley & Sons, Inc., N.Y., N.Y., 3rd ed., 1983).

R. E. Anderson, "Ion Exchange Separations", *Handbook of Separation Techniques for Chemical Engineers*, Section 1.12, McGraw-Hill, New York, N.Y., 1979.

C. J. Brown and C. J. Fletcher, "The Recoflo Short Bed Ion Exchange Process", Streat, *Ion Exchange for Industry*, pp. 392-403, Ellis Horwod Ltd., Chichester, England, 1979.

Amberlite® Ion Exchange Resins, Fluid Process Chemicals and Apparatus.

Hatch and Dillon, "Process Design and Development", 1963, pp. 253-263.

Chemical Engineers' Handbook, 5th Edition.

METHODS FOR RECOVERY OF ACIDS

CROSS-REFERENCE TO RELATED APPLICATIONS

This application is a continuation-in-part of U.S. Ser. No. 08/115,382, filed Sep. 1, 1993, now abandoned.

FIELD OF THE INVENTION

This invention relates to a process for recovering sulfuric acid from a mixture containing sulfuric acid and organic sulfonation products.

BACKGROUND OF THE INVENTION

The recovery of mineral acids from mixtures is generally known. B. A. Bolto and L. Pawlowski, *Wastewater Treatment by Ion Exchange*, pp. 49–56 (E. & F. N. Spoon, Ltd, N.Y., N.Y., 1987), describe the use of ion exchange resins to separate acids from salts by acid retardation, e.g. the separation of iron sulfate salts from sulfuric acid in exhausted steel pickling solutions. Bolto also states that ion-exchange methods can be use for the recovery of various organic compounds from wastes, citing for example, the separation of sulphonic and sulfuric acids. Bolto cites as an example the separation of 5-sulfoisophthalic acid from sulfuric acid as described by R. C. Glogau, "Separate Sulfonic and Sulfuric Acids with an Ion Exchange Resin", *Industrial and Engineering Chemistry*, vol. 53, pp. 275–278 (April 1961).

Glogau et al. states that the separations of sulfuric acid from 5-sulfoisophthalic acid, from benzenesulfonic acid and from p-toluenesulfonic acid were studied. Most of the work was done with 5-sulfoisophthalic acid and Dowex 1-X16. Glogau et al. state they studied the effect of degree of crosslinking of the resin from Dowex 1-X7.5 to 1-X24 (i.e. from 7.5% to 24% divinylbenzene crosslinking agent) and found that acid capacity decreased with increasing crosslinking and in several cases the 5-sulfoisophthalic acid was virtually excluded.

An early Dow technical bulletin, "Chemical Processing By Ion Exchange", Form No. 17 424, pp. 1–18 (Dow Chemical U.S.A., Midland, Mich.) describes, at page 2, the Dowex 1 series of resins as Type I strong base anion exchange resins. The Dow bulletin further states that the Dowex 1 series is of the gel type made from styrene and divinyl benzene. The Dow bulletin discusses acid retardation at pages 12 and 13. It is stated that acid retardation permits separation of strong acids from their salts by passing the solution through the corresponding salt from of Dowex 1X8 or Dowex 21K, strong base anion exchange resin, for example passing a strong solution of hydrochloric acid and sodium chloride through the chloride form of Dowex 1X8. The Dow bulletin goes on to state at page 13 that the procedure has been used to separate free sulfuric acid from sulfonated oils, particularly when more highly crosslinked resins are used.

A later Dow technical bulletin, "Dowex Ion Exchange Resins; Powerful Chemical Processing Tools", Form. No. 177-1395-87, pp. 1–12 (Dow Chemical U.S.A., Midland, Mich.) notes at page 9 that mixtures of sulfuric acid and its salts are separated by passage through a bed of Dowex M-41 resin which selectively imbibes the acid moiety relative to the salt. Dowex M-41 is a type I strongly basic anion exchange resin having a macroreticular (or macro-porous) structure. (Macroreticular is a term employed in literature from Rohm & Haas regarding ion exchange resins; the term "macroporous" is employed by most other manufacturers of ion exchange resins.)

British Patent GB-1,264,293 describes the use of macro-reticular ion exchange resins to remove sulfuric acid from oil-soluble sulfonic acids. It is stated at page 2, lines 4–14, that the process is restricted to the oil-soluble sulfonic acids and that such acids, in order to be considered oil-soluble, generally require that the hydrocarbon portion of the sulfonic acid have a molecular weight between 350 and 1,000, and that examples of the oil-soluble sulfonic acids are alkaryl hydrocarbons having the required molecular weight, e.g. those derived from benzene, toluene, xylene or naphthalene. In the process, the oil-soluble sulfonic acid is in a hydrocarbon solvent and regeneration of the resin is accomplished by washing with water.

SUMMARY OF THE INVENTION

This invention relates a process for the separation of sulfuric acid from a mixture, said process comprising:

contacting a mixture comprised of sulfuric acid and a naphthalene-based material selected from the group consisting of naphthalenesulfonic acids, lower-alkyl substituted naphthalenesulfonic acids, and mixtures of two or more of such materials, with a basic anion exchange resin in essentially the sulfate form (and preferably in the form of essentially nonporous particles) to provide a raffinate liquid phase enriched with respect to said mixture in said naphthalene-based material and depleted with respect to said mixture in sulfuric acid;

removing said raffinate liquid phase from contact with said basic anion exchange resin;

contacting said basic anion exchange resin with an aqueous liquid at an essentially neutral pH to form an extract liquid phase consisting essentially of sulfuric acid;

and removing said extract liquid phase from contact with said basic anion exchange resin.

This invention also relates a process for the separation of sulfuric acid from a mixture, said process comprising:

contacting a mixture comprised of sulfuric acid and an aromatic-based carbonyl condensate (preferably a material selected from the group consisting of formaldehyde condensates of naphthalenesulfonic acids, formaldehyde condensates of lower-alkyl substituted naphthalenesulfonic acids, and mixtures of two or more of such materials), with a basic anion exchange resin in essentially the sulfate form (and preferably in the form of essentially non-porous particles) to provide a raffinate liquid phase enriched with respect to said mixture in said naphthalene-based material and depleted with respect to said mixture in sulfuric acid (and preferably depleted in arylsulfonic acids);

removing said raffinate liquid phase from contact with said basic anion exchange resin;

contacting said basic anion exchange resin with an aqueous liquid at an essentially neutral pH to form an extract liquid phase consisting essentially of sulfuric acid;

and removing said extract liquid phase from contact with said basic anion exchange resin.

DETAILED DESCRIPTION OF THE INVENTION

The first step in the process of this invention involves contacting a mixture comprised of sulfuric acid and a naphthalene-based material selected from the group consisting of naphthalene sulfonic acids, lower-alkyl substituted naphthalenesulfonic acids, and mixtures of two or more of such materials, or an aromatic-based carbonyl condensate, with a basic anion exchange resin. The naphthalene-based material will be water soluble. In the context of naphthalenesulfonic acid and lower alkyl substituted naphthalenesulfonic acids, this means that the material will have a molecular weight below about 350. Examples of lower alkyl naphthalenesulfonic acids which will be useful herein are those wherein the total of the carbon atoms in the alkyl groups will be less than 16. Such examples include methyl naphthalenes, ethyl naphthalenes, iso-propyl naphthalenes, di-isopropyl naphthalenes, butyl naphthalenes.

The naphthalene-based material will typically be a mixture of chemical species. For example, the naphthalene will typically be derived from coal tar or a petroleum base that will contain naphthalene and one or more lower-alkyl naphthalenes. Further, the sulfonation of the naphthalene base will typically produce a mixture containing some di-sulfonated naphthalenes and/or some un-sulfonated naphthalenes. The sulfonation of naphthalene is described by E. A. Knaggs, "Sulfonation and Sulfation", *Encyclopedia of Chemical Technology*, vol. 2, p. 1–45 (John Wiley & Sons, Inc., N.Y.,N.Y., 3rd ed., 1983), the disclosure of which is incorporated herein by reference.

In an other aspect, the mixture from which sulfuric acid is separated will be an aromatic based condensate of a condensable carbonyl compound, i.e. an aromatic-based carbonyl condensate. Preferred examples of such condensates are the formaldehyde condensates of naphthalenesulfonic acids and formaldehyde condensates of lower-alkyl substituted naphthalenesulfonic acids. Sulfonated naphthalenes can be employed in the manufacture of naphthalene formaldehyde condensates. As an alternative to pre-sulfonation, the naphthalene base can be sulfonated during the condensation with formaldehyde. Such condensation produces a product that can be considered naphthaleneformaldehyde sulfonic acid and is also known as the naphthalenesulfonic acid-formaldehyde condensates, formalin condensates of betanaphthalenesulfonic acid, condensation products of naphthalenesulfonic acid with formaldehyde. Naphthaleneformaldehyde sulfonic acid may be prepared by reacting a mixture of naphthalene, formaldehyde and sulfuric acid or oleum. It may be prepared by the processes described in U.S. Pat. No. 2,141,569 (Tucker et al, issued Dec. 27, 1938), U.S. Pat. No. 3,193,575 (Nebel et al, issued Jul. 6, 1965), and U.S. Pat. No. 3,277,162 (Johnson, issued Oct. 4, 1966).

Naphthaleneformaldehyde sulfonic acid is a mixture of condensation products of naphthalenesulfonic acid and formaldehyde, such condensation products differing, for example, in the degree of polymerization. It can be chromatographed by size exclusion chromatography through a column containing pore sizes which selectively separate molecular volumes according to size, thus allowing one to obtain a measure of the degree of polymerization. The solvent chosen for the acid in chromatography should minimize solute-packing interaction and solute-solute interaction. The chromatogram gives a true molecular volume profile when the eluents are displayed on a detector-strip chart recorder display. For example, if the chromatogram for a sample of the sulfonic acid is the same as that for the sodium naphthaleneformaldehyde sulfonate in U.S. Pat. No. 3,954,491 (Adrian et al, issued May 4, 1976), the two anionic materials are identical. That is, the anionic materials from the acid have the same profile as the anionic materials from the sodium naphthaleneformaldehyde sulfonate having lowest elution volumes of from above 61 to about 70% of the total elution volume and equivalent elution volumes of from about 61 to about 70% of the total elution volume. The teachings in U.S. Pat. No. 3,954,491 relating to chromatography are incorporated by reference herein. Typical resins will have a number average molecular weight of from about 2,000 to about 4,000 and a weight average molecular weight of from about 7,000 to about 13,000 and will contain from 1–5% by weight of non-condensate impurities.

Other examples of aromatic-based carbonyl condensates include the condensation products of acetone with naphthalenesulfonic acid. The method of this invention is also useful, at least when it employs a type A weak base anion resin of the macroreticular type, in removing from an aromatic-based carbonyl condensate, e.g. naphthalene-formaldehyde condensate, arylsulfonic acids, e.g. alpha-naphthalenesulfonic acid, betanaphthalenesulfonic acid, and/or other low molecular weight impurities that are typically present in a crude reaction product at a nominal concentration (e.g. a concentration of from about 1% to about 5%, more typically from about 2 to about 3%).

The naphthalene-based material will typically be the product of a sulfonation reaction, i.e. the reaction of a naphthalene-based reactant with a sulfonating agent, e.g. concentrated sulfuric acid or oleum. As such, the naphthalene-based material will typically contain only a minor amount of water, e.g. only the water produced as a by-product of the sulfonation reaction (optionally with any water present in the formaldehyde that may be employed in a condensation reaction). Such minor amounts will generally range from about 1% to about 30% by weight. Typically, the mixture will also be comprised of only a minor amount of sulfuric acid, e.g. from about 1% to about 30%, but the amount of sulfuric acid may vary broadly.

The first step of the process is to contact the mixture with a basic anion exchange resin. Ion exchange resins and their use are described by R. E. Anderson in Section 1.12, "Ion exchange Separations", in P. A. Schweitzer (ed.), *Handbook of Separation Techniques for Chemical Engineers* (McGraw-Hill, New York, 1979) the disclosure of which is incorporated by reference herein. It has been found that the use of such a resin in an essentially non-porous form, e.g. a gel type resin, is particularly useful in obtaining a high degree of selectivity for the sulfuric acid from an alkyl-substituted naphthalenesulfonic acid such as (diisopropyl)naphthalenesulfonic acid. An essentially non-porous resin can be characterized as a resin of the gel type, i.e. the resin is in the form of a crosslinked gel wherein essentially the only pores within the gel are the distances between the polymeric chains within the gel. Such resins are to be contrasted with macro-reticular resins which contain non-gel porosity, typically as non-gel interstices between agglomerates of minute spherical gel particles. The degree of crosslinking of the resin may vary, but it has been found that a degree of crosslinking of from 1% to 7% (expressed as the weight percent of divinyl benzene reacted into the resin) is particularly useful, e.g. such a resin was the most selective in the separation of sulfuric acid from (di-isopropyl)naphthalenesulfonic acid. The basic ion exchange resin typically will be in the form of beads (e.g. having mesh sizes from about 10 to about 100, more typically 20 mesh to 50 mesh) or powders (e.g. having mesh sizes from about 80 to about 250 mesh, more typically from 100 mesh to 150 mesh).

The basic anion exchange resin can be of the weak base type or the strong base type. Conventional weak base resins are characterized as being amine functional resins of one of four types. Type S weak base resins are similar to the type I strong base resins in that they are based on the chloromethylation of a styrene resin followed by reaction with a secondary amine, e.g. dimethyl amine. Such resins typically have some strong base (quaternary amine) functionality when manufactured, which functionality typically decreases upon cycling of the resin. Type P weak base resins are based on phenol-formaldehyde polymers with weak base functionality of the polyalkyleneamine type. Type E resins are produced by the reaction of epichlorohydrin with a polyalkyleneamine. Type A weak base resins are based on polyacrylates with the amine functionality (i.e. a mono-, di- or poly-amine) bonded to the polymer structure by an ester or amide linkage.

The strong base anion exchange resin will typically have quaternary amine functionality. For example, type I strong base resins based on styrene have a N,N,N-trimethyl N-benzyl amine group and are typically prepared by chloromethylation of a styrene resin followed by reaction with a tertiary amine. Type II resins based on styrene have a N,N-dimethyl N-hydroxyethyl N-benzyl amine group.

The basic anion exchange resin will be (at least partially) in its sulfate form, i.e. wherein the counter-ion of the quaternary ammonium functionality is a sulfate anion. It is possible to use a resin wherein a portion of the counter-ions are an anion that is displaced by the bisulfate anion from the sulfuric acid in the mixture to be separated. However, this displaced anion will most probably elute (at least partially) with the naphthalene-based material thereby reducing the purity of the naphthalene-based material. Thus, the resin will typically have, prior to contact with the mixture from which sulfuric acid is to be separated, a predominant amount of the basic functionality of the resin associated with a sulfate counter-ion. The resin is most preferably placed in essentially completely its sulfate form prior to its use. This can be accomplished for strong base resins by displacement of the original counter-ion (e.g. chloride) with sulfate, e.g. an alkali metal sulfate such as sodium sulfate. Conversion of a weak base resin to the sulfate form will typically entail the use of sulfuric acid, typically dilute (e.g. 5% by weight sulfuric acid in water) sulfuric acid in an amount greater than the stoichiometric equivalence of the weak base resin (e.g. from about 150% to 200% of the stoichiometric equivalence).

Upon contact with the resin, the mixture provides a raffinate liquid phase depleted (with respect to said mixture) in sulfuric acid. The raffinate is depleted in sulfuric acid in the sense that the weight ratio of sulfuric acid to naphthalene-based material or aromatic-based carbonyl condensate will be greater than said ratio of the starting mixture. The raffinate liquid will typically be correspondingly enriched in naphthalene-based material or aromatic-based carbonyl condensate, at least on a water-free basis (the naphthalene-based material or aromatic-based carbonyl condensate may be at a lower absolute concentration due to dilution with free water in the resin, e.g. water remaining from a preceding cycle of operation).

It is believed that the sulfuric acid in the mixture diffuses into the gel structure of the resin and dissociates which causes (i) protonation of sulfate counter-ions of the resin and (ii) the formation of bisulfate ions which tend to associate with the quaternary amine groups. This diffusion thus causes the liquid phase outside of the resin particles to be enriched (with respect to said mixture) in said naphthalene-based material (by diffusion of the acid therefrom). The liquid phase can then be characterized as a raffinate liquid phase. It has been noted, however, that protonation of the sulfate counter-ions is probably not the only mechanism by which passage of the sulfuric acid through the bed of resin because the separation achieved is greater, typically several (e.g. 2 to 3) times greater, than the theoretical maximum based solely on protonation of the sulfate functionality. Thus, the invention generally contemplates the addition to the bed of sulfuric acid in an amount greater than the stoichiometric equivalency of the basic ion exchange resin, preferably at least 150% of the stoichiometric equivalency, prior to desorption of the sulfuric acid with water. Because the resin is in the sulfate form, conventional ion exchange is not possible.

The raffinate will typically contain only a minor portion, by weight, of the sulfuric acid present in the mixture, i.e. less than 50% by weight of the sulfuric acid originally present will remain in the raffinate. Thus, the contacting step will be effective in removing a major portion, by weight of the sulfuric acid in the mixture, i.e. at least 50%, typically from about 75% to about 95%.

The removal of said raffinate liquid phase from contact with said basic anion exchange resin is then effected. Such a removal is performed by physical means and the precise means of such removal will depend upon the operating regime chosen for the separation. After removal of the raffinate liquid phase from contact with the resin, the resin is then contacted with an aqueous liquid at an essentially neutral pH. Such contact will form an extract liquid phase consisting essentially of sulfuric acid as an extract liquid phase. The process is then completed by removing said extract liquid phase from contact with said basic anion exchange resin.

The separation can be performed by a variety of operating techniques or regimes, e.g. batch processing, fixed-bed (preferably semi-continuous in a pulsed mode), and moving-bed (e.g. in a simulated counter-current mode). The preferred mode employs a fixed bed of resin. The mixture to be separated is introduced into the fixed bed in a pulse followed by a pulse of elution water. This pulsing will set up a concentration gradient along the column so that a raffinate effluent can be collected from the other end of the column first, a recycle effluent will be collected next and an acid extract will be collected last. The sequence of pulses are then continued such that the separation is effected in a semi-continuous manner.

Conventional ion exchange apparatus can be used to perform the process of the invention. Examples of such apparatus are described by Bolto, above. It may be advantageous to employ an ion exchange apparatus as described by C. J. Brown and C. J. Fletcher, "The Recoflo Short Bed Ion Exchange Process", in Streat, *Ion Exchange for Industry*, pp.392–403 (Ellis Horwood Ltd., Chichester, England) and the citations noted therein, particularly U.S. Pat. No. 4,673,507 (Brown), the disclosures of which are incorporated herein by reference. Brown discloses an apparatus and process for treating a fluid by passing the fluid through a bed of particulate material such as an ion exchange resin capable of taking up from the fluid a component to be removed therefrom. Substantially uniform fluid flow distribution across the cross-sectional area of the bed is achieved by employing resins of fine particle size which are maintained in an overpacked condition.

The formation of the extract liquid phase may be sufficiently slow that steps to speed up such extract formation may be desirable. Such steps include the use of a basic anion exchange resin with a relatively smaller particle size and/or operating the separation in such a manner to achieve a reciprocating flow. Such reciprocating flow can be accomplished by introducing the aqueous liquid with an essentially neutral pH into the resin bed to achieve an extract flow that is counter-current to the raffinate flow, e.g. by feeding the mixture to be separated to the top of the resin bed, withdrawing raffinate from the bottom of the resin bed, introducing the aqueous liquid with an essentially neutral pH into the bottom of the resin bed, and then withdrawing extract from the top of the resin bed.

The raffinate will typically be a high solids material that will need, at most, only minimal processing to be sold as a useful article of commerce. For example, it may be most efficient to remove only a portion of the sulfuric acid in the mixture and to neutralize the remaining portion of sulfuric acid, e.g. with an alkali an/or alkaline earth base, e.g. sodium hydroxide, soda ash, or calcium oxide or hydroxide. The extract will typically be a dilute sulfuric acid solution. This dilute solution can be concentrated for recycling to a sulfonation or sale as an article of commerce.

The following examples are intended to illustrate the invention without limiting it in any way.

EXAMPLES

Batch Procedure

A series of ion exchange resins were prepared and evaluated for recovery of sulfuric acid according to the following procedure. About 100 ml of ion exchange resin were placed in a beaker to which was added about 200 to 250 ml of sodium sulfate (5% by weight in deionized water) to the strong base resins and 200 to 250 ml of sulfuric acid (5% by weight in deionized water) to the weak base resins. The resulting slurry was mixed for 5 minutes and allowed to sit (e.g. overnight) before decantation of the liquid. Two separate aliquots of additional sodium sulfate solution or sulfuric acid were sequentially added and decanted in the same manner.

The resin was then washed by slurrying with about 200 ml deionized water and mixing for 10 minutes followed by decantation of the liquid, and rewashed twice in the same manner. About 50 ml of washed resin was then filtered on a Buchner funnel, weighed and transferred to a jacketed 100 ml beaker (with circulating water at 70° C. in the jacket). About 50 ml of the sulfuric acid mixture were weighed, pre-heated to 70° C., and added to the beaker with magnetic stirring.

After 30 minutes, the contents of the beaker were filtered and the filtrate was weighed. The resin was the washed with 50 ml of ambient temperature deionized water and filtered to collect a second filtrate which was weighed. The resin was then washed again with 50 ml of ambient temperature deionized water and filtered to collect a third filtrate. The selectivity of the separation for sulfuric acid can be calculated as the product of (i) the ratio of the concentration of sulfuric acid in the resin phase at equilibrium to the concentration of the sulfuric acid in the bulk liquid phase at equilibrium and (ii) the ratio of the concentration of sulfonic acid in the liquid phase at equilibrium to the concentration of the sulfonic acid in the resin phase at equilibrium. Selectivity can be described as the ratio of species in the extract phase divided by the same ratio of species in the raffinate phase.

Column Procedure

Fill a jacketed glass column with 1 cm. inside diameter and 100 cm in length (78.5 cc volume) with about 75 cc of anion exchange resin. Load through a water phase at about 70° C. (so that air does not evolve and create bubbles when the column is heated during operation). Exchange the resin to the sulfate forming by pumping through several bed volumes (BV) of dilute (5% by weight) aqueous sodium sulfate solution for strong base resins or several bed volumes of dilute (5% by weight) aqueous sulfuric acid for weak base resins. Fill a jacketed vessel with the sulfuric acid/sulfonic acid mixture and another jacketed vessel with deionized water. Heat the jacketed vessels and column to 70° C. with a circulating water bath. Begin pumping deionized water from the jacketed vessel upflow through the column at 2 BV per hour (2.5 cc/min.) to allow for inspection for bubbles or other irregularities. At time zero, turn off the deionized water pump and turn on the sulfuric acid/sulfonic acid feed pump. Pump one-third ($\frac{1}{3}$) BV of feed (25 cc) upflow through the column a 2 BV per hour (2.5 cc/min.). Then turn off the feed pump and turn on the deionized water pump at 2 BV per hour (2.5 cc/min.). At time zero, begin collecting 10 samples of column effluent, each sample comprising about 0.25 BV (18–20 cc). Then collect 2 samples of column effluent, each sample comprising about 0.5 BV (36–40 cc). Carefully weigh the samples bottles before and after filling. Analyze effluent for water (by Karl Fischer titration method), sulfate anion by anion liquid chromatography, and sulfonation product by gel permeation chromatography.

Resins

It should be noted that the percent of crosslinking (% crosslinking) set forth below is the percent by weight of the multi-ethylenic monomer, e.g. divinylbenzene, in the resin polymer.

Resin A: a strong base (type I, 0.8 meq/ml), acrylic/divinylbenzene (6% crosslinking) resin in macroreticular form, available from Rohm and Haas Co., Phila. Pa., as Amberlite IRA-958.

Resin B: a strong base (type I), styrene/divinylbenzene (6% crosslinking) resin in macroreticular form, available from Dow Chemical U.S.A., Midland, Mich., as Dowex M-41.

Resin C: a strong base (type I, 1.0 meq/ml), styrene/divinylbenzene (4% crosslinking) resin in macroreticular form, available from Rohm and Haas Co., Phila. Pa., as Amberlite IRA-900.

Resin D: a strong base (type I), styrene/divinylbenzene (10% crosslinking) resin in mono-bead gel form, available from Dow Chemical U.S.A., Midland, Mich., as Dowex G-55.

Resin E: a strong base (type I, 1.4 meq/ml), styrene/divinylbenzene (3% crosslinking) resin in gel form, available from Rohm and Haas Co., Phila. Pa., as Amberlite IRA-400.

Resin F: a weak base (1.2 meq/ml) anion exchange resin, styrene/divinylbenzene (3–4% crosslinking) resin in macroreticular form, available from Rohm and Haas Co., Phila. Pa., as Amberlite IRA-93.

Resin G: a weak base (1.6 meq/ml) anion exchange resin, acrylic/divinylbenzene (6% crosslinking) resin in gel form, available from Rohm and Haas Co., Phila. Pa., as Amberlite IRA-68.

Resin H: a weak base (1.3 meq/ml) anion exchange resin, styrene/divinylbenzene resin in macroreticular form, available from Rohm and Haas Co., Phila. Pa., as Amberlyst A-21.

Resin I: a strong base (type I, 1.0 meq/ml) anion exchange resin, styrene/divinylbenzene (4% crosslinking) resin in macroreticular form, available from Rohm and Haas Co., Phila. Pa., as Amberlyst A-26.

Resin J: a strong base (type I, 0.7 meq/ml) anion exchange resin, styrene/divinylbenzene (20% crosslinking) resin in macroreticular form, available from Rohm and Haas Co., Phila. Pa., as Amberlyst A-27.

Resin K: a strong base (type II) anion exchange resin, styrene/diviinylbenzene (4% crosslinking) resin in macroreticular form, available from Rohm and Haas Co., Phila. Pa., as Amberlyst A-29.

Resin L: a strong base (type I) anion exchange resin, styrene/divinylbenzene resin in gel form, available from Dianex (U.S. subsidiary of Mitsubishi, Japan), as Diaion SA-10A.

Examples 1–5

Five separate aliquots of a crude sulfonation product mixture of (diisopropyl)naphthalenesulfonic acid (DIPNSA) at 78.9% by wt. of the mixture, sulfuric acid (12.1% by wt.) and water (9.0% by wt.) were treated according to the batch procedure set forth above, each with one of the resins and with the results shown below (wherein raffinate is abbreviated "RAFF.").

TABLE 1

| RESIN | RAFF. WT % DIPNSA | RAFF. WT % $H_2SO_4$ | RAFF. WT % $H_2O$ | % $H_2SO_4$ in RAFF. (Water Free Basis) | WT. % $H_2SO_4$ Reduced | DIPNSA Adsorbed #/ft$^3$ | $H_2SO_4$ Adsorbed #/ft$^3$ | Resin Selectivity |
|---|---|---|---|---|---|---|---|---|
| A | 47.1 | 6.3 | 46.6 | 11.8 | 12.8 | 21.9 | 4.0 | 1.36 |
| B | 54.5 | 6.1 | 39.4 | 10.1 | 27.0 | 17.7 | 4.4 | 2.22 |
| C | 63.1 | 4.3 | 32.6 | 6.4 | 55.6 | 9.9 | 4.9 | 7.26 |
| D | 70.4 | 2.1 | 27.5 | 2.9 | 80.6 | 6.5 | 7.7 | 39.7 |
| E | 74.6 | 1.4 | 24.0 | 1.8 | 87.8 | 2.9 | 7.4 | 136.0 |

Examples 6–17

A mixture of a mono-sulfonated-naphthalene formaldehyde condensate (said condensate having a weight average molecular weight, $M_w$, of about 9,000 to about 11,000, a number average molecular weight, $M_n$, of about 3,000, and less than about 5% by weight of disulfonates and other condensate species) having a sulfuric acid content of about 25% by weight can be divided into 24 separate aliquots. One of each of 12 aliquots can be treated according to the batch procedure set forth above with one each of Resins A through L, set forth above. One each of the remaining 12 aliquots can be treated according to the column procedure set forth above with one each of Resins A through L, set forth above.

What is claimed is:

1. A process for the separation of sulfuric acid from a mixture, said process comprising:
   contacting a liquid mixture comprised of sulfuric acid and a water soluble naphthalene-based material selected from the group consisting of naphthalenesulfonic acids, lower-alkyl substituted naphthalenesulfonic acids, and mixtures thereof, with a basic anion exchange resin in essentially the sulfate form to provide a raffinate liquid phase depleted with respect to said mixture in sulfuric acid;
   removing said raffinate liquid phase from contact with said basic anion exchange resin;
   contacting said basic anion exchange resin with an aqueous liquid at an essentially neutral pH to form an extract liquid phase consisting essentially of sulfuric acid;
   and removing said extract liquid phase from contact with said basic anion exchange resin.

2. A process for the separation of sulfuric acid from a mixture, said process comprising:
   contacting a liquid mixture comprised of sulfuric acid and a water soluble aromatic-based carbonyl condensate with a basic anion exchange resin in essentially the sulfate form to provide a raffinate liquid phase depleted with respect to said mixture in sulfuric acid;
   removing said raffinate liquid phase from contact with said basic anion exchange resin;
   contacting said basic anion exchange resin with an aqueous liquid at an essentially neutral pH to form an extract liquid phase consisting essentially of sulfuric acid;
   and removing said extract liquid phase from contact with said basic anion exchange resin.

3. A process of claim 2 wherein said aromatic-based carbonyl condensate is a material selected from the group consisting of formaldehyde condensates of naphthalenesulfonic acids, formaldehyde condensates of lower-alkyl substituted naphthalenesulfonic acids, and mixtures of two or more of such materials.

4. A process of claim 2 wherein said basic anion exchange resin is in the form of essentially non-porous particles.

5. A process of claim 2 wherein sulfuric acid is present in said mixture in an amount greater than the stoichiometric equivalent of said basic anion exchange resin.

6. A process of claim 2 wherein said aromatic-based carbonyl condensate has a number average molecular weight of from about 2,000 to 4,000 and a weight average molecular weight of from about 7,000 to about 13,000.

7. A process of claim 2 wherein said mixture of sulfuric acid and aromatic-based carbonyl condensate is further comprised of water in a minor amount by weight.

8. A process of claim 2 wherein said mixture of sulfuric acid and aromatic-based carbonyl condensate is further comprised of from about 1% to 30% by weight of water.

9. A process of claim 2 wherein the amount of said sulfuric acid in said mixture of sulfuric acid and aromatic-based carbonyl condensate is at least 150% of the stoichiometric equivalent of said basic anion exchange resin.

10. A process of claim 2 wherein said basic anion exchange resin is a macroreticular resin.

11. A process of claim 2 wherein said basic anion exchange resin is a weak base resin.

12. A process of claim 2 wherein said basic anion exchange resin is a strong base resin.

13. A process of claim 2 wherein said basic anion exchange resin has a degree of crosslinking of from 1% to 7%.

14. A process of claim 2 wherein said basic anion exchange resin is in the form of beads.

15. A process of claim 2 wherein said basic anion exchange resin is in the form of a powder.

16. A process of claim 2 wherein the amount of sulfuric acid in said mixture of sulfuric acid and aromatic-based carbonyl condensate is a minor amount by weight.

17. A process of claim 2 wherein the amount of sulfuric acid in said mixture of sulfuric acid and aromatic-based carbonyl condensate is from 1% to 30% by weight of said mixture.

18. A process of claim 2 wherein said raffinate liquid phase contains sulfuric acid in an amount of less than about 50% by weight of the sulfuric acid present in said mixture of sulfuric acid and aromatic-based carbonyl condensate.

19. A process of claim 2 wherein said raffinate liquid phase contains sulfuric acid in an amount of from about 5% to 25% by weight of the sulfuric acid present in said mixture of sulfuric acid and aromatic-based carbonyl condensate.

20. A process of claim 1 wherein said basic anion exchange resin is contained in a fixed bed and the sequence of said contacting with said mixture of sulfuric acid and naphthalene-based material and said contacting with an aqueous liquid as an essentially neutral pH is continued such that the separation is effected in a semi-continuous manner.

21. A process of claim 1 wherein said basic anion exchange resin is contained in a fixed bed and said aqueous liquid at an essentially neutral pH is introduced into the bed to achieve an extract flow that is counter-current to the flow of said raffinate.

22. A process of claim 1 wherein said resin is in the form of essentially nonporous particles.

23. A process of claim 1 wherein sulfuric acid is present in said mixture in an amount greater than the stoichiometric equivalent of the basic ion exchange resin.

24. A process of claim 1 wherein said naphthalene-based material has a number average molecular weight of less than about 350.

25. A process of claim 1 wherein said mixture of sulfuric acid and naphthalene-based material is further comprised of water in a minor amount by weight.

26. A process of claim 1 wherein said mixture of sulfuric acid and naphthalene-based material is further comprised of from about 1% to 30% by weight of water.

27. A process of claim 1 wherein the amount of said sulfuric acid in said mixture of sulfuric acid and naphthalene-based material is at least 150% of the stoichiometric equivalent of said basic anion exchange resin.

28. A process of claim 1 wherein said basic anion exchange resin is a macroreticular resin.

29. A process of claim 1 wherein said basic anion exchange resin is a weak base resin.

30. A process of claim 1 wherein said basic anion exchange resin is a strong base resin.

31. A process of claim 1 wherein said basic anion exchange resin has a degree of crosslinking of from 1% to 7%.

32. A process of claim 1 wherein said basic anion exchange resin is in the form of beads.

33. A process of claim 1 wherein said basic anion exchange resin is in the form of a powder.

34. A process of claim 1 wherein the amount of sulfuric acid in said mixture of sulfuric acid and naphthalene-based material is a minor amount by weight.

35. A process of claim 1 wherein the amount of sulfuric acid in said mixture of sulfuric acid and naphthalene-based material is from 1% to 30% by weight of said mixture.

36. A process of claim 1 wherein said raffinate liquid phase contains sulfuric acid in an amount of less than about 50% by weight of the sulfuric acid present in said mixture of sulfuric acid and naphthalene-based material.

37. A process of claim 1 wherein said raffinate liquid phase contains sulfuric acid in an amount of from about 5% to 25% by weight of the sulfuric acid present in said mixture of sulfuric acid and naphthalene-based material.

38. A process of claim 1 wherein said naphthalene-based material is selected from the group of naphthalenesulfonic acid and lower-alkyl substituted naphthalenesulfonic acids wherein the total number of carbon atoms in the alkyl groups of said lower-alkyl substituted naphthalenesulfonic acids is less than 16.

39. A process of claim 1 wherein said naphthalene-based material is further comprised of di-sulfonated naphthalenes.

40. A process of claim 1 wherein said naphthalene-based material is the product of the sulfonation of a coal tar base or petroleum base.

41. A process of claim 1 wherein said basic anion exchange resin is contained in a fixed bed and the sequence of said contacting with said mixture of sulfuric acid and naphthalene-based material and said contacting with an aqueous liquid as an essentially neutral pH is continued such that the separation is effected in a semi-continuous manner.

42. A process of claim 1 wherein said basic anion exchange resin is contained in a fixed bed and said aqueous liquid at an essentially neutral pH is introduced into the bed to achieve an extract flow that is counter-current to the flow of said raffinate.

* * * * *